United States Patent
Ash et al.

[11] Patent Number: 5,947,953
[45] Date of Patent: Sep. 7, 1999

[54] SPLITTABLE MULTIPLE CATHETER ASSEMBLY AND METHODS OF INSERTING THE SAME

[75] Inventors: Stephen R. Ash, West Lafayette, Ind.; Anthony J. Madison, Fort Washington; Timothy M. Schweikert, Levittown, both of Pa.

[73] Assignees: HemoCleanse, Inc., West Lafayette, Ind.; Medical Components, Inc., Harleysville, Pa.

[21] Appl. No.: 08/907,311

[22] Filed: Aug. 6, 1997

[51] Int. Cl.⁶ .................................................. A61M 31/00
[52] U.S. Cl. ......................... 604/508; 604/43; 604/264; 138/115; 138/117
[58] Field of Search ................................ 604/43, 53–54, 604/93, 264, 280, 283, 284, 540, 541, 508; 138/115, 117

[56] References Cited

U.S. PATENT DOCUMENTS

| | | |
|---|---|---|
| 2,286,462 | 6/1942 | Chaffin . |
| 3,144,868 | 8/1964 | Jascalevich . |
| 4,072,153 | 2/1978 | Swartz . |
| 4,405,313 | 9/1983 | Sisley et al. . |
| 4,568,329 | 2/1986 | Mahurkar . |
| 4,583,968 | 4/1986 | Mahurkar . |
| 4,692,141 | 9/1987 | Mahurkar . |
| 4,808,155 | 2/1989 | Mahurkar . |
| 4,925,452 | 5/1990 | Melinyshyn et al. ............... 604/284 |
| 5,120,299 | 6/1992 | Lombardi ................................ 600/18 |
| 5,197,951 | 3/1993 | Mahurkar . |
| 5,221,255 | 6/1993 | Mahurkar et al. . |
| 5,236,016 | 8/1993 | Vogelsang ............................. 138/115 |
| 5,318,517 | 6/1994 | Reiman . |
| 5,338,308 | 8/1994 | Wilk . |
| 5,374,245 | 12/1994 | Mahurkar . |
| 5,405,341 | 4/1995 | Martin . |
| 5,785,686 | 7/1998 | Runge ...................................... 604/96 |
| 5,800,414 | 9/1998 | Cazal ..................................... 604/280 |

FOREIGN PATENT DOCUMENTS 0 386 408   1/1990   European Pat. Off. .

Primary Examiner—Wynn Wood Coggins
Assistant Examiner—LoAn H. Thanh
Attorney, Agent, or Firm—Panitch Schwarze Jacobs & Nadel, P.C.

[57] ABSTRACT

A multiple lumen catheter assembly and methods for inserting the same are provided. The assembly includes a splittable membrane joining a first catheter and a second catheter for allowing the catheters to be at least partially longitudinally split from each other. Each catheter has at least one lumen extending longitudinally through the catheter. One method for inserting the assembly includes making an incision near the area to be catheterized, at least partially splitting the distal end regions of the catheters from each other by splitting apart the splittable membrane, and inserting the distal end regions of the catheters in a juxtaposed relation through the incision and into the area to be catheterized. In another method, the catheters are first tunnelled subcutaneously by pulling the distal end regions of the catheters in the assembly through a tunnel and outwardly from the tunnel near the area to be catheterized, leaving proximal end regions at least partially within the tunnel. An incision is made near the area to be catheterized, the distal end regions of the catheters are at least partially split from each other by splitting the splittable membrane, and the distal end regions of the catheters are inserted in a juxtaposed relation through the incision and into the area to be catheterized.

24 Claims, 7 Drawing Sheets

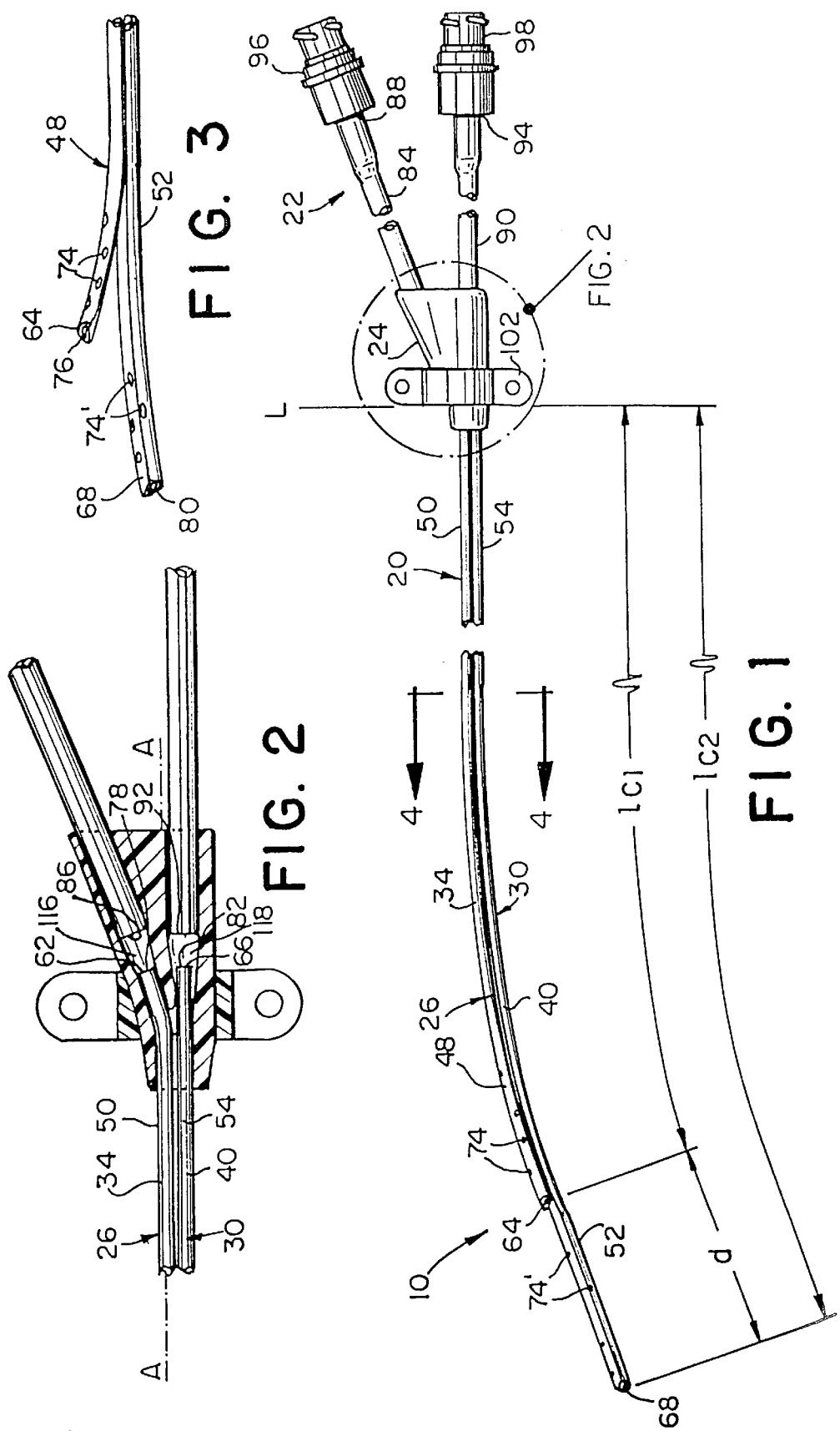

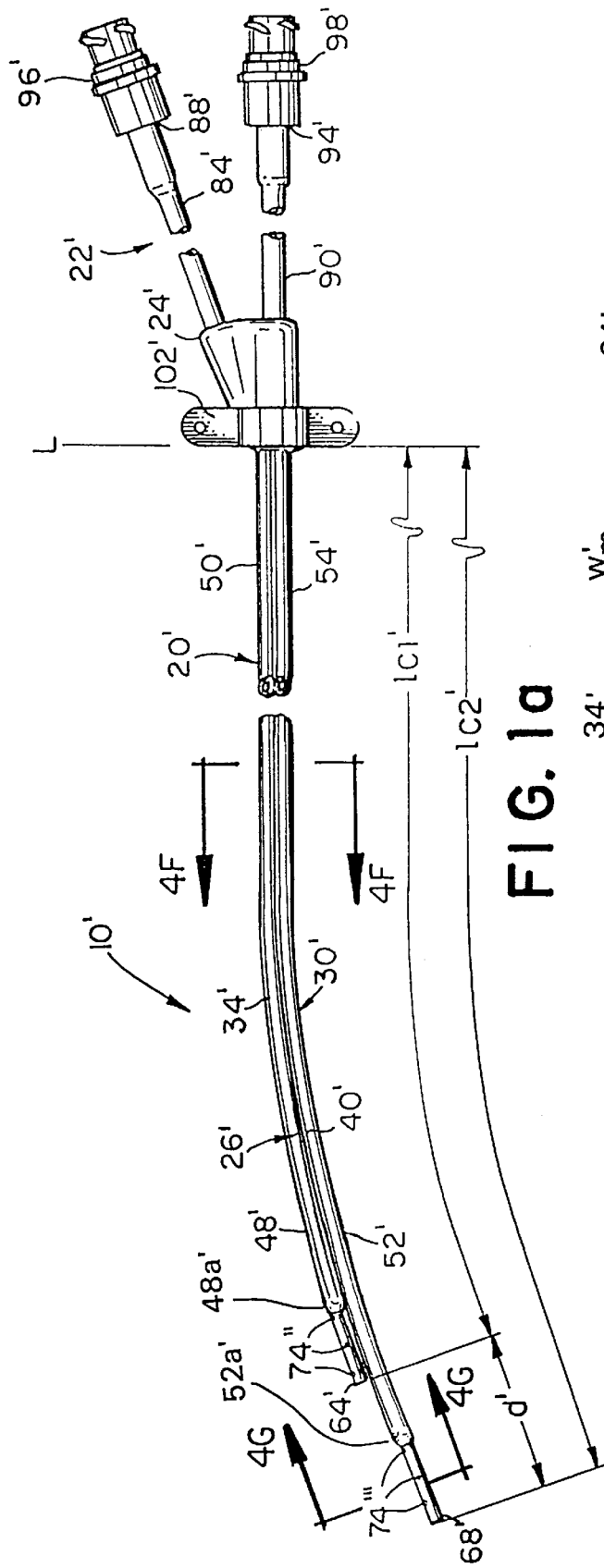
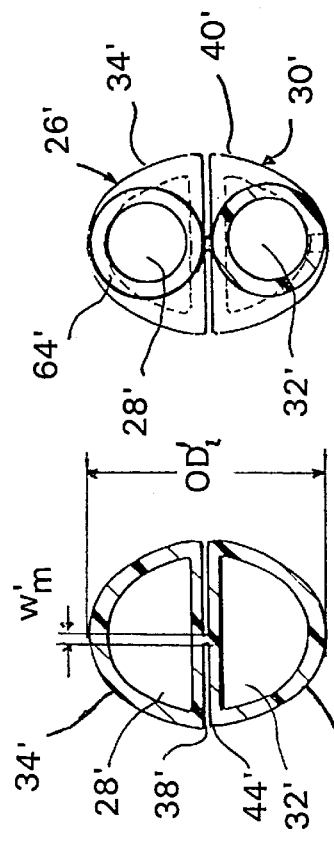
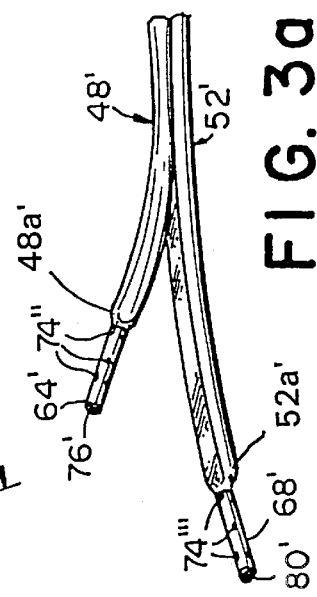
FIG. 1a
FIG. 4F
FIG. 4G
FIG. 3a

SPLITTABLE MULTIPLE CATHETER ASSEMBLY AND METHODS OF INSERTING THE SAME

BACKGROUND OF THE INVENTION

Catheters for the introduction or removal of fluids may be located in various venous locations and cavities throughout the body for the introduction or removal of fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Such multiple catheter assemblies are known as Tesio catheters.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through a syringe needle or other introducer device, into the interior of the vessel. The introducer device is then removed leaving the guide wire within the vessel. The guide wire projects beyond the surface of the skin.

At this point, several options are available to a physician for catheter placement. The simplest is to pass a catheter into the vessel directly over the guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

In the case of an individual, single-lumen catheter typically used in multiple catheter assemblies (e.g., a Tesio catheter), a physician may use an introducer sheath. If a Tesio is used for hemodialysis, for example, each catheter is inserted in two separate veins, such as the femoral vein. Alternatively, each catheter may be inserted in two different locations of the same vein, such as the internal jugular vein. The introducer sheath is simply a large, stiff thin-walled tube which serves as a temporary conduit for the permanent catheter which is being placed. The introducer sheath is positioned by placing a dilator device inside of the introducer and passing both the dilator and the introducer together into the vessel over a guide wire. The guide wire, left in the vessel after insertion as described above, and the dilator are then removed, leaving the thin-walled introducer sheath in place. The catheter is placed through the introducer sheath. Each of the catheters in the assembly is typically subcutaneously secured within the patient's body by a cuff located in a subcutaneous tunnel, or by otherwise externally affixing the catheter to the body.

The Tesio catheter may also be inserted in accordance with the technique described in U.S. Pat. No. 5,624,413 through a single insertion point using a sheath into the vessel. The Tesio, once inserted in the vessel, is then tunnelled separately through the patient in two subcutaneous tunnels for securement of the external, proximal portions of the catheter.

The Tesio double catheter assembly, while comfortable for the patient, due to its soft durometer, and very effective for hemodialysis, typically requires multiple procedures and incisions, which increase the attendant risks of the catheterization procedure. However, the Tesio double catheter assembly provides catheters which are capable of independent movement within the vessel. Such catheters present several advantages over unitary multi-lumen catheters. Because they are independently movable at their fluid outlets, it is possible to provide fluid intake and/or return flow around the entire circumference of the distal ends of the catheter tubes. In addition, if one tube becomes blocked, or otherwise requires replacement, it can be removed independently of the other tube. Further, the softer durometer of such catheters, which are typically made of a silicone or a similar material, reduces the risk of vessel wall damage. The 360° circumferential flow provides a more stable tube within the vessel, which is less likely to be suctioned against the vessel wall due to a pressure differential, as occasionally occurs in the use of some side-by-side multi-lumen catheters.

One recent catheter design, the SchonCath® catheter, available from Medical Components, Inc. of Harleysville, Pa., provides a partially connected Tesio. The individual catheters are permanently linked in one portion by a retaining sleeve for self-anchoring under the skin, as an alternative to requiring a fabric stabilizing cuff, such that such cuffs are optional. The distal ends are longitudinally prespaced by an appropriate distance to avoid recirculation. The retaining sleeve fits snugly around the individual catheters, and is positioned at a location along the length of the catheters to be situated outside the vessel wall, under the skin between the beginning of the subcutaneous tunnels and the vessel insertion site. While this device requires only one incision, it requires two subcutaneous tunnels in order to facilitate the self-retaining feature. This catheter provides independently movable distal ends within the vessel and 360° circumferential flow in the manner of a standard Tesio.

There is a need in the art for a multiple lumen catheter which provides the advantages of a multi-lumen catheter's single insertion and a single tunneling procedure, and which also provides the advantages of the Tesio and SchonCath® catheters.

SUMMARY OF THE INVENTION

The present invention relates generally to a multiple catheter assembly and methods for inserting the catheter assembly into an area within the body to be catheterized.

The invention includes a multiple catheter assembly, comprising a first catheter, a second catheter and a splittable membrane. The first catheter has a proximal tip, a distal end region terminating in a distal tip, and an outer surface defining at least a first lumen extending longitudinally therethrough between a distal and a proximal opening. The second catheter has a proximal tip, a distal end region terminating in a distal tip, and an outer surface defining at least a second lumen extending longitudinally therethrough between a distal and a proximal opening, wherein the first lumen and the second lumen are independent from each other for facilitating flow in opposite directions. The splittable membrane joins the outer surfaces of both the first and second catheters for allowing the first and second catheters to be at least partially longitudinally split from each other.

The invention further includes a method for inserting a multiple catheter assembly into an area of a body to be catheterized. The assembly comprises (i) a first catheter having a proximal end region terminating in a proximal tip, a distal end region terminating in a distal tip, and an outer surface defining at least a first longitudinally extending lumen, (ii) a second catheter having a proximal end region terminating in a proximal tip, a distal end region terminating in a distal tip, and an outer surface defining at least a second longitudinally extending lumen, wherein the first lumen and the second lumen are independent from each other for facilitating flow in opposite directions, and (iii) a splittable membrane joining the outer surfaces of both the first and second catheters. The method comprises the steps of making an incision near the area to be catheterized, at least partially splitting the distal end regions of the first catheter and the second catheter from each other by splitting the splittable membrane; and inserting the distal end regions of the first and second catheters in juxtaposed relation through the incision and into the area to be catheterized.

The invention further includes an alternative method of inserting a multiple catheter assembly into an area of a body to be catheterized. The assembly comprises (i) a first catheter having a proximal end region terminating in a proximal tip, a distal end region terminating in a distal tip, and an outer surface defining at least a first longitudinally extending lumen, (ii) a second catheter having a proximal end region terminating in a proximal tip, a distal end region terminating in a distal tip, and an outer surface defining at least a second longitudinally extending lumen, wherein the first lumen and the second lumen are independent from each other for facilitating flow in opposite directions, and (iii) a splittable membrane joining the outer surfaces of both the first and second catheters. The method comprises the steps of subcutaneously moving the first and second catheters through a tunnel formed in the body by pulling the distal end regions through the tunnel and outwardly therefrom near the area to be catheterized, leaving the proximal end regions at least partially within the tunnel. An incision is made near the area to be catheterized, and the distal end regions of the first and second catheters are at least partially split from each other by splitting the splittable membrane. The distal end regions of the first and second catheters are inserted in juxtaposed relation through the incision and into the area to be catheterized.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, the same reference numerals are employed for designating the same elements throughout the several figures. In the drawings:

FIG. 1 is a perspective view of a multiple catheter assembly in accordance with an embodiment of the present invention;

FIG. 1a is a perspective view of a multiple catheter assembly in accordance with a preferred embodiment of the present invention;

FIG. 2 is an enlarged view of a portion of FIG. 1;

FIG. 3 is a perspective view of a portion of the multiple catheter assembly of FIG. 1, showing the assembly in a partially split state;

FIG. 3a is a perspective view of a portion of the multiple catheter assembly of FIG. 1a, showing the assembly in a partially split state;

FIG. 4F is an enlarged cross-sectional view of the multiple catheter assembly of FIG. 1a, taken along line 4F—4F;

FIG. 4G is an enlarged cross-sectional view of the multiple catheter assembly of FIG. 1a, taken along line 4G—4G;

DETAILED DESCRIPTION OF THE INVENTION

Figure 4A:
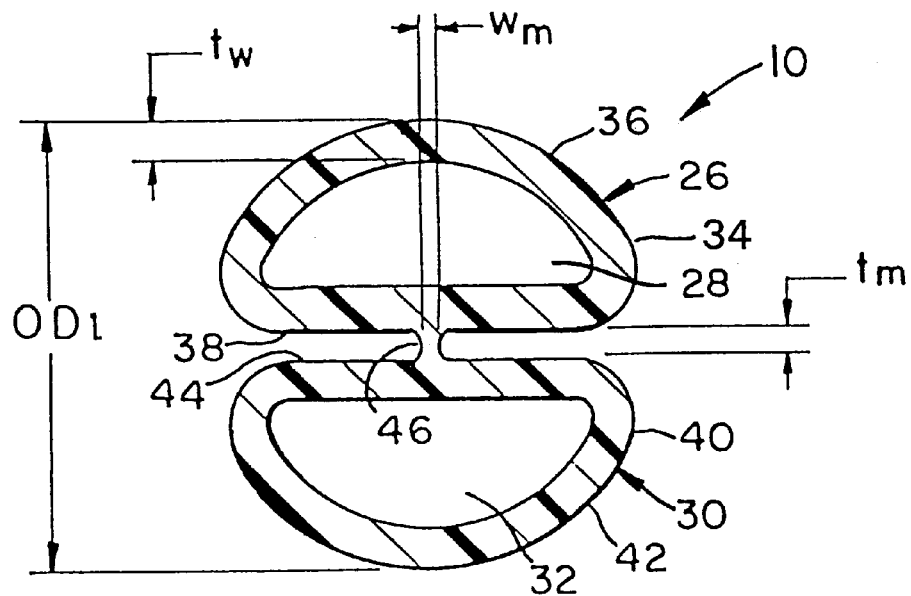
FIG. 4A is an enlarged cross-sectional view of the multiple catheter assembly of FIG. 1, taken along line 4—4.

Certain terminology is used herein for convenience only and is not to be taken as a limitation on the present invention. The words "right," "left," "outwardly" and "inwardly" designate directions in the drawings to which reference is made. The words "proximal" and "distal" refer to directions away from and closer to, respectively, the insertion tips of the first and second catheters in the multiple catheter assembly according to the present invention. The terminology includes the words above specifically mentioned, derivatives thereof, and words of similar import.

The following describes preferred embodiments of the invention. However, it should be understood, based on this disclosure, that the invention is not limited by the preferred embodiments described herein. Referring now to the drawings in detail, there are shown in FIGS. 1–4A, embodiments of a multiple catheter assembly generally indicated as 10, 10'. The catheter assembly 10 shown in FIGS. 1, 2, 3 and 4A is a double catheter assembly, although assemblies having three or more catheters are within the scope of the invention. Similarly, the catheter assembly 10' shown in FIGS. 1a, 3a, 4F and 4G, which represents a preferred embodiment according to the present invention, is shown and described herein as a double catheter assembly having a modified distal region as described further below, but also may have three or more catheters within the scope of the invention. The embodiments of FIGS. 1 and 1a are in most respects the same and a general reference and description concerning the embodiment of FIGS. 1, 2, 3 and 4A also applies with respect to the preferred embodiment of FIGS. 1a, 3, 4F and 4G, unless specifically noted herein. Notably, the distal end regions of the catheters 10, 10' are different in their cross-sectional configurations and the placement of the circumferential openings in those regions. These features are described further below with specific reference to FIGS. 1, 3, 4F and 4G.

Figure 5:
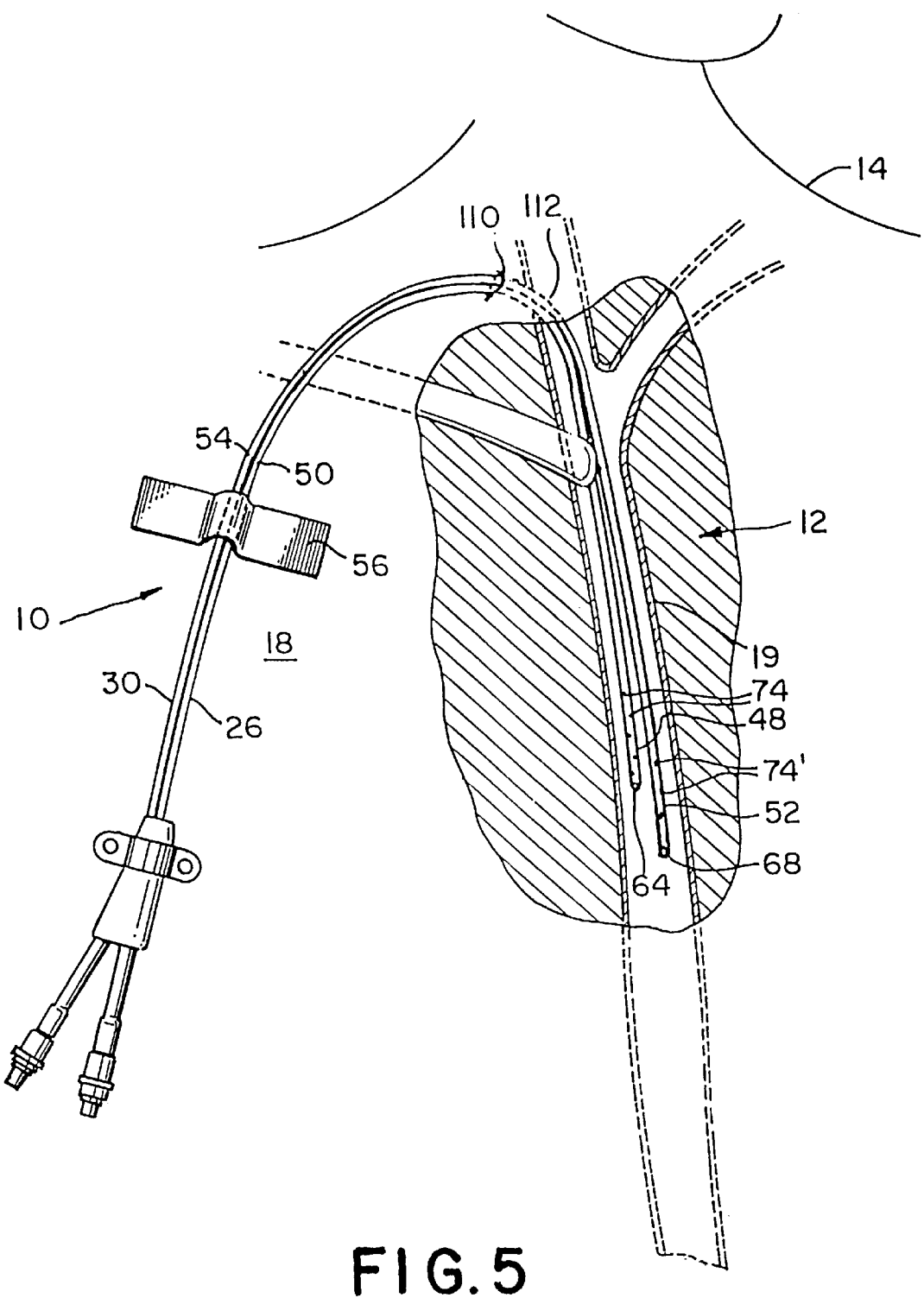
FIG. 5 is a partially broken-away diagrammatic view of a multiple catheter assembly which has been partially split and inserted into an area to be catheterized, in accordance with one embodiment of a method of inserting a multiple catheter assembly according to the present invention.
Figure 6:
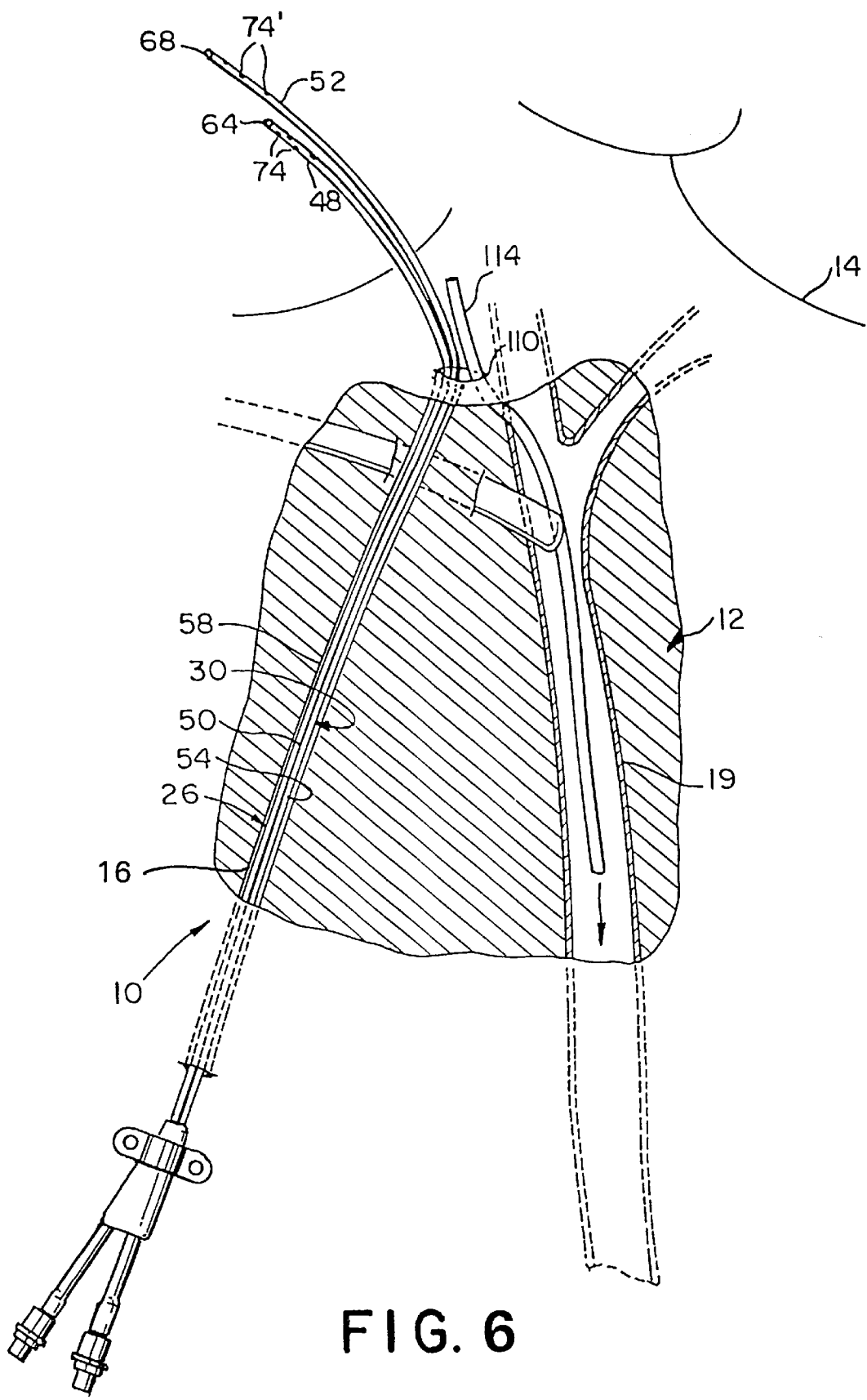
FIG. 6 is a partially broken-away diagrammatic view of the split catheter assembly subcutaneously tunnelled in a body and insertion into an area to be catheterized, in accordance with an alternative method of inserting a multiple catheter assembly.
Figure 7:
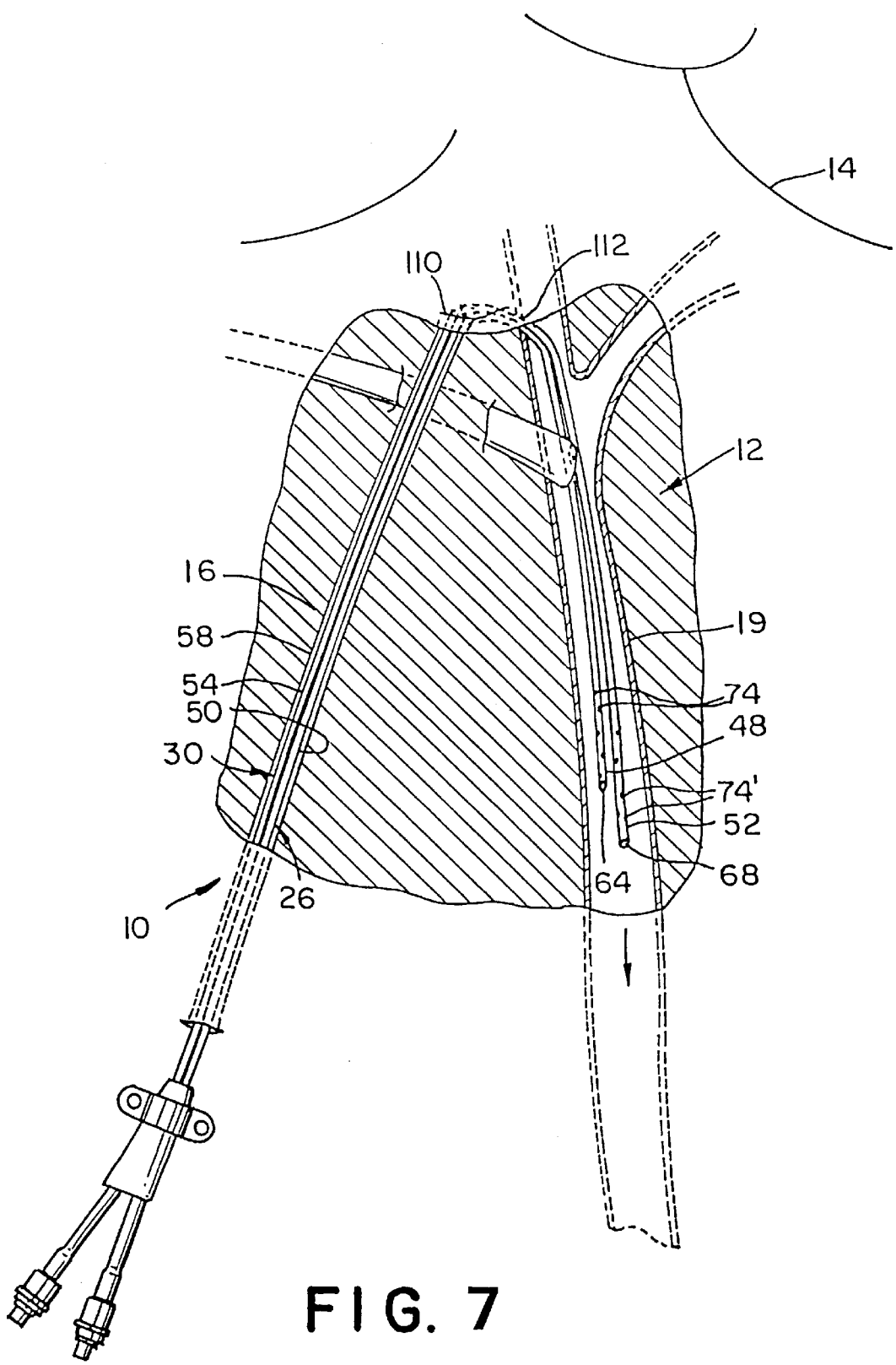
FIG. 7 is a partially broken-away diagrammatic view of a multiple catheter assembly of FIG. 6 wherein the distal end regions of the catheters are inserted into the area to be catheterized.

Referring to FIGS. 5–7, and as described in further detail below, a catheter assembly according to the present invention is inserted into an area 12 of a body 14 for removing and introducing fluids to the area 12. While either embodiment of FIG. 1 or 1a may be used in the manner shown in FIGS. 5–7, the use of the assembly and method of the present invention are described with reference to a catheter assembly 10 for convenience purposes as it would be difficult to show the distal tip detail of the embodiment of FIG. 1a in FIGS. 5–7. The catheter assembly 10 is secured to a fixed location in or on the body 14, such as a subcutaneous area 16, as shown in FIG. 6, in the body 14 before it is properly inserted and positioned in the catheterization area 12. This method is particularly preferred for chronic catheterization. Alternatively, and preferably for acute catheterization, the catheter assembly 10 is secured to an external surface 18 of the body 14, as shown in FIG. 5, before or after it is properly inserted and positioned in the catheterization area 12.

The catheter assembly of the present invention 10, 10' can be adapted for use in various applications in which bodily fluids, medicaments or other solutions are introduced into and removed from the body such as perfusion, infusion, plasmapheresis, hemodialysis, chemotherapy, and the like. The area to be catheterized is preferably a blood vessel such as an internal jugular vein, but may be any suitable area within the body. Other areas in which the catheter assembly may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 10, 10' may be used to remove or introduce fluids in various areas to be catheterized.

The embodiments of the invention as shown in FIGS. 1 and 1a, are preferably useful for intake, or removal, of blood to be purified from a blood vessel, such as the internal jugular vein, and introduction of purified blood into the same vessel. The blood can be purified by any suitable hemodialysis apparatus (not shown) attached in communication with the lumens of the catheter assembly of the invention 10, 10'. The catheters may also be used to introduce medication or other fluids including glucose or saline solutions into the body.

For the purposes of describing the preferred embodiment of the present invention, the device will be described with respect to the preferred application of hemodialysis, more specifically, for purifying blood flowing through the internal jugular vein 19. However, it will be understood by one skilled in the art based on this disclosure, that the assembly 10, 10' can be configured and adapted, by increasing or decreasing the catheter size and/or number of catheters and/or lumens in the assembly, such that the assembly 10, 10' can be beneficially used for other medical applications in which fluids are introduced into and/or removed from the body.

Referring now to the embodiment of FIGS. 1–4A, the multiple catheter assembly 10 includes a cannulating portion 20 which is generally on the left side of an imaginary dividing line L, and an optional extension tube portion 22 which is generally on the right side of line L. The cannulating portion 20 is preferably joined to the extension tube portion 22 by a hub 24, as described in more detail below. A first catheter 26 has an outer surface 34 defining a first lumen 28 as best shown in FIG. 4A extending longitudinally through the catheter. The second catheter 30 has an outer surface 40 defining a second lumen 32 extending therethrough as best shown in FIG. 4A. The first and second lumens 28, 32 extend through the full length of their respective catheters 26, 30.

As shown in FIG. 4A, the lumens 28, 32 preferably each have a generally semi-circular cross section. Accordingly, the catheter 26 has an outer surface 34 defined by a rounded wall portion 36 and a generally flat side surface 38, as viewed in cross section, and the catheter 30 also has an outer surface 40 defined by a rounded wall portion 42 and a generally flat side surface 44, as viewed in cross section. The generally flat side surfaces 38, 44 preferably face each other. The generally flat side surfaces 38 and 44 do not touch each other, but are very close. Also, it is preferred that the lumens 28, 32 and respective rounded wall portions and generally flat side surfaces 38, 44 are identical to each other so that the cannulating portion 20 of the catheter assembly 10 has a generally circular cross section. It should be understood, however, based on this disclosure, that the lumens may be further subdivided and/or additional catheter tubes of the same or varied cross sectional configuration can be provided including, if necessary, additional membranes, within the scope of the invention. A similar cross sectional configuration is shown for the embodiment of FIG. 1a in FIG. 4F.

The catheter assembly 10 includes a splittable membrane 46 which extends longitudinally between and joins the opposite generally flat side surfaces 38, 44 of the first and second catheters 26, 30. It is preferred that the membrane 46 extends between the central line of the flat side surfaces 38, 44 for dimensional stability. However, the membrane 46 could extend between edges of the side surfaces 38, 44 or between other regions of the flat side surfaces 38, 44 or rounded wall portions 36, 42.

The membrane 46 performs multiple functions. First, the membrane 46 joins the first and second catheters 26, 30 so that the catheters 26, 30 can be easily manipulated, particularly along the section of the catheters 26, 30 where the membrane 46 is unbroken. If the membrane 46 is completely intact, the catheters 26, 30 can be manipulated as a single catheter. Second, the membrane 46 allows the first and second catheters 26, 30 to be at least partially longitudinally split apart from each other, as shown in FIG. 3, without damaging the outer surfaces 34, 40 of either of the first or second catheters 26, 30, thereby allowing independent movement of the split end regions in the vessel or other area to be catheterized. The membrane 46 is constructed to split easily when the first and second catheters 26, 30 are forcibly separated from each other. It is preferred, as shown, for example, in FIGS. 4A and 4F, that the membrane 46 has a cross-sectional width at its thinnest portion $w_m$ which is a very small fraction of the outer diameter $OD_1$ of the catheter assembly 10 to facilitate easy tearing. The membrane 46 is also preferably constructed of a material which will tear before the forces exerted on the outer surfaces 34, 40 of either of the first or second catheters 26, 30 reach a level sufficient to cause damage thereto. However, the membrane material should be sufficiently strong to resist tearing during normal handling of the assembly 10. The membrane 46 has a cross-sectional length $t_m$ which is also a small fraction of the outer diameter $OD_1$ of catheter assembly 10. The cross-sectional length $t_m$ also defines the distance between the generally flat side surfaces 38, 44. The cross-sectional distance $t_m$ is preferably small to maintain an overall generally circular cross section for the unseparated section of the catheter assembly 10 and to facilitate handling of the unseparated section of the catheter assembly 10 in the cannulating portion 20.

While the dimensions may be varied for different size catheters and embodiments of this invention, in the embodiment shown in FIG. 1, as described, for example, for a 13.5 FR catheter assembly, the catheter assembly 10 would preferably have an approximate cross-sectional wall thickness $t_w$ for the rounded wall portions 36, 42, of about 0.015 in. to about 0.017 in. The cross-sectional width $w_m$ of the membrane 46, at its thinnest portion, as measured in a direction parallel to the flat side surfaces 38, 44 would preferably be from about 0.005 in. to about 0.007 in. The cross-sectional length $t_m$ of the membrane 46 as measured in a direction perpendicular to the flat side surfaces 38, 44 would preferably be about 0.011 in. The outer diameter $OD_1$ of the catheter assembly 10 of the exemplary 13.5 FR catheter assembly, as measured in the transverse direction in the cannulating portion 20 would be preferably from about 0.165 in. to about 0.173 in.

The length $l_{c1}$, for the same exemplary 13.5 FR catheter, as measured between the distal tip 64 and proximal tip 62 of the first catheter 26 would be preferably about 6.82 in.±0.250 in. and the length $l_{c2}$ as measured between the distal tip 68 and the proximal tip 66 of the second catheter 30 would preferably be about 8.0 in.±0.50 in. The length of the extension tubes 84, 90, for such a catheter assembly, as measured between their respective distal ends 86, 92 and proximal ends 88, 94 would preferably be about 2.750 in.±0.125 in. The distal tips 64, 68 of the catheters 26, 30 are preferably separated by a distance d of 1.6 in. (i.e., about 4 cm) prior to splitting. The distance which the first and second catheters 26, 30 are generally split from each other prior to use is about 3 cm. The catheters are preferably partially split prior to use to facilitate forming holes 74, 74' in the distal end regions 48, 52 of the catheters.

While the generally semi-circular cross section as shown in FIG. 4A and in FIG. 4F, corresponding to the cross-sectional configuration of assembly 10' of FIG. 1a, is the preferred configuration for fluid flow in each lumen 28, 32, other configurations may be used without departing from the spirit of the present invention, such as, for example, oval, circular, elliptical, square, triangular and kidney-bean shaped. The catheter assembly 10 when having such luminal configurations will have a varied cross section accordingly.

The lumens 28, 32 may be of equal cross-sectional or of different cross-sectional areas. For example, a lumen having a small cross sectional area in comparison with the first and second lumens may be used for infusion of medication. The catheter assembly will also not be circular in cross section in the configuration having unequal cross-sectional areas.

Figure 4E:
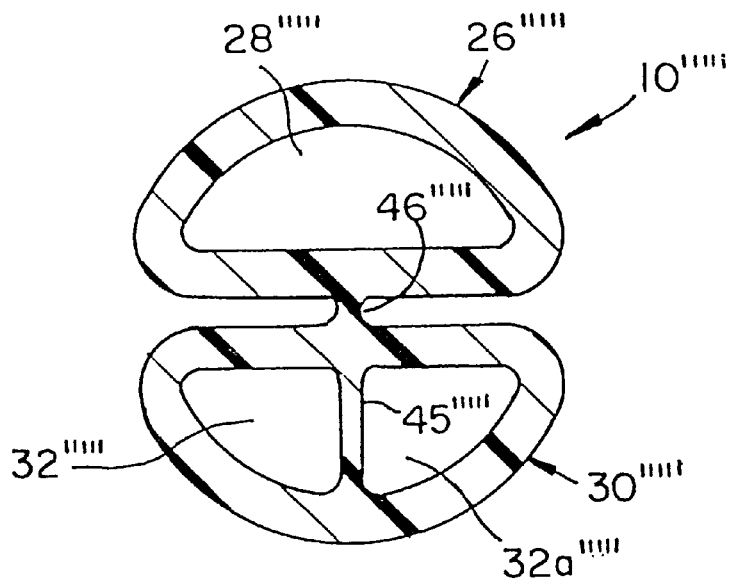
FIGS. 4B–4E are enlarged cross-sectional views of multiple catheter assemblies in accordance with additional embodiments of the present invention.
Figure 4B:
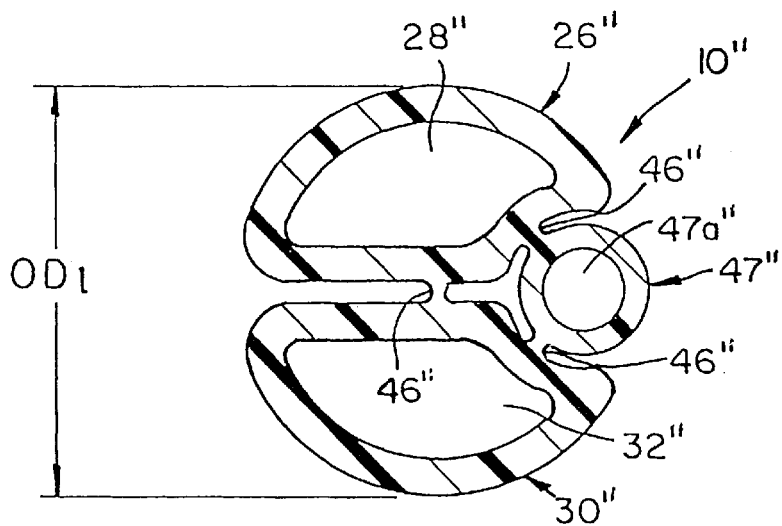

While two lumens of equal cross section are shown in FIG. 4A, additional catheters having lumens of the same or different cross-sectional areas may also be included in a multiple catheter assembly of the embodiments of FIGS. 1 and 1a for use in the present invention. For example, as shown in FIG. 4B, a multiple catheter assembly 10" for hemodialysis may have two catheters 26", 30" with lumens 28", 32" of equal cross-sectional area for removal and return of blood and a third catheter 47" having a third lumen 47a" of a smaller circular cross sectional area for infusion of medication. In such an embodiment, the catheters may be interconnected by three splittable membranes 46".

Figure 4C:
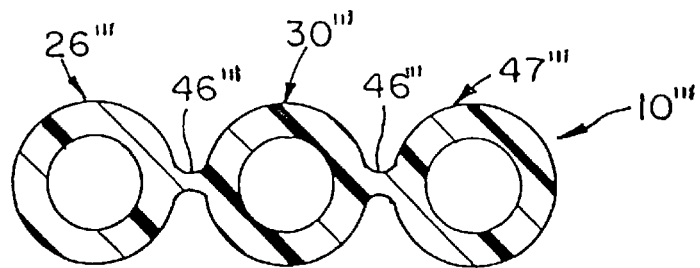
Figure 4D:
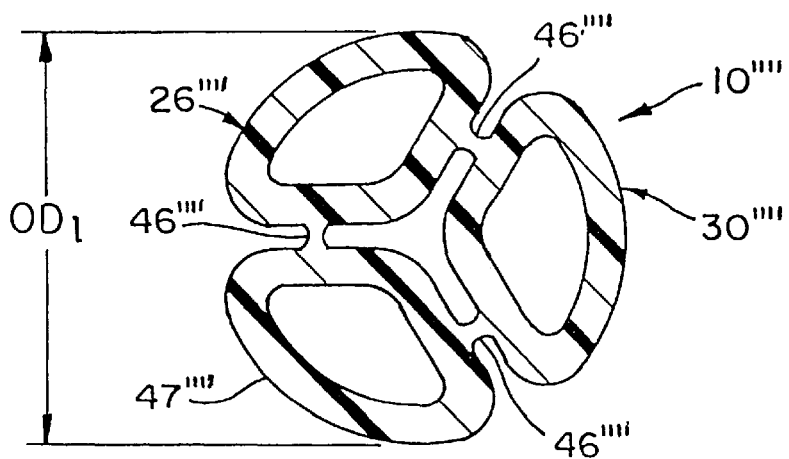

If more than two catheter tubes are provided to the assembly, there should be more than one splittable membrane to interconnect the catheters. There may be additional splittable membranes associated with various multiple lumen catheter assemblies. For example, there may be an assembly 10''' with two splittable membranes 46''' associated with a triple tube catheter assembly in which three catheters 26''', 30''', 47''' are arranged in a juxtaposed fashion as shown in FIG. 4C. There may also be a catheter assembly 10'''', as shown in FIG. 4D having three arcuate and generally triangular catheters 26'''', 30'''', 47'''' and an overall generally circular cross section. The catheters 26'''', 30'''', 47'''' have three splittable membranes 46'''' interconnecting the three catheters. The membranes allow for at least partially longitudinally splitting the catheters from each other.

It is also possible to subdivide the various catheter tubes within the assembly by providing at least one longitudinally extending septum within a tube. In this manner, for example, as shown in FIG. 4E, two catheter tubes 26''''', 30''''' having one splittable membrane 46''''' can provide three independent lumens by having a first lumen 28''''' in one catheter tube 26''''' and two lumens 32''''', 32a''''' separated by a septum 45''''' in the other catheter tube 30''''' as shown in FIG. 4E.

Examples of such alternative tube configurations of the catheter assembly 10 as shown in FIGS. 4B-4E, which may also be used in the catheter assembly 10' of FIG. 1a, are intended to be exemplary only with respect to the versatility and possible various configurations achievable with the present invention. It will be understood, based on this disclosure, however, that the present invention is not limited to the configurations shown in FIGS. 4A-4G, The first catheter 26 and the second catheter 30 are all preferably made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheters 26, 30, it is most preferred that the polymeric material includes a polyurethane or a polyolefin polymeric material having a preferably soft durometer, as specified below.

Suitable, preferred, biocompatible elastomers for use in forming the catheters 26, 30 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 26, 30 are made of the elastomeric material such that they are flexible, durable, soft, and easily conformable to the shape of the area to be catheterized 12 and/or the subcutaneous area 16 and minimize risk of harm to vessel walls. If the catheters 26, 30 are used for hemodialysis applications, they are preferably formed of a soft silicone elastomer which has a hardness of at least about 80-A on a Shore durometer scale. Such an elastomer is available from Dow Corning, and can include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 26, 30 may also be radiopaque depending on their intended use.

Referring to again to FIGS. 1–7, the first catheter 26 includes a distal end region 48 and a proximal end region 50. Likewise, the second catheter 30 includes a distal end region 52 and a proximal end region 54. The distal end regions 48, 52 are configured to be placed, or inserted into, the area to be catheterized 12, whereas the proximal end regions 50, 54 remain outside of the area 12.

In a preferred embodiment of one method of inserting a catheter according to the present invention as shown in FIG. 5, described herein with respect to the embodiment of FIG. 1 for convenience purposes, the proximal end regions 50 and 54 may be secured to the skin 18 of the body 14 by a suitable fastening material 56, such as adhesive tape, after the catheter assembly 10 is properly inserted in the area 12. This method of securing and positioning the catheter assembly 10 is typically used in emergency or acute catheterization.

In another embodiment of the present invention method as shown in FIGS. 6–7, the respective proximal end regions 50 and 54 may be secured in a subcutaneous area such as a subcutaneous tunnel 16 formed through the body 14 and typically extending between a subcutaneous area near the area of insertion into, for example, a vessel and a caudal exit site. Methods of tunnelling are known to those of ordinary skill in the art. Tunnelling may be used for in either chronic or acute procedures.

In addition, as shown in FIGS. 1 and 2, the first catheter 26 has a proximal tip 62 at the furthest end of its proximal end region 50 and a distal tip 64 at the furthest end of its distal end region 48. Likewise, the second catheter 30 has a proximal tip 66 at the furthest end of its proximal end region 54 and a distal tip 68 at the furthest end of its end region 52. The distal end regions 48, 52 are provided with a plurality of apertures 74, 74'. The function of the apertures 74, 74' is described in more detail below. The first catheter 26 also has a distal opening 76 extending through the distal tip 64 and a proximal opening 78 extending through the proximal tip 62. Likewise, as shown in FIG. 3, the second catheter 30 has a distal opening 80 extending through the distal tip 68 and a proximal opening 82 extending through the proximal tip 66.

The distal tips 64, 68 as shown in FIG. 1 and 3 are blunt, in that they are configured to lie generally in a plane which is perpendicular to the longitudinal axis A—A of the catheter assembly 10, and have a semi-cylindrical cross section. As shown in FIGS. 2 and 3, the distal tips 64, 68 may alternatively be slightly rounded (not shown). However, in the preferred embodiment of the present invention as shown in FIG. 1a, the distal tips 64', 68', while blunt, have a circular cross section. It is preferred that a portion of the distal end regions 48', 52' each have a transition point 48a', 52a' at which the outer surfaces 34', 40' of the first and second catheters 26', 30' are rounded inwardly between the generally semi-cylindrical cross section of the main portion of the catheters 26', 30' and the generally circular cross section of the portions of the distal end regions 48', 52' adjacent the distal tips 64', 68'. The holes 74" and 74'", which correspond to the holes 74' and 74" in FIG. 1, are preferably formed in the portion of the distal end regions 48', 52' having the circular cross section.

This configuration is also shown in FIGS. 4F and 4G. As shown in FIG. 4F, the cross section of the main body of the cannulating portion 20' is generally circular in outer diameter $OD_1$ and the septum has a width $w_m'$ which corresponds to $W_m$ of catheter assembly 10 of FIG. 1–4A. All other relevant dimensions for this portion of the catheter also may be found in catheter assembly 10'. In FIG. 4G, the cross section of the portion of the distal end regions 48', 52' having a generally circular cross section is shown. The outer surfaces are rounded inwardly primarily on the curved wall portions 26', 32' of the outer surfaces 34', 40' of the catheters. The flat side surfaces 38', 44' gradually converge more smoothly into the generally circular cross section portions of the distal end regions 48', 52'.

With reference to both embodiments as shown in FIGS. 1 and 1a (but referring generally to FIG. 1 for convenience), the distal tips 64, 68 are preferably integral with the catheter body as shown in both embodiments of the assembly 10, 10', and the catheters are preferably integrally molded. By configuring the distal tips 64, 68 in a blunt design, regardless of whether the distal end regions undergo transition from a generally semi-circular to a generally circular configuration as in FIG. 1a, and forming the entire catheter from a soft material such as a silicone elastomer, trauma to the area 12 and stenosis are minimized. It should be understood from this disclosure that while blunt tips are preferred, other tip configurations may be used in the present method, such as, for example, tapered tips for facilitating insertion or for accommodating other potential applications of the assembly 10. However, such tapered designs are not preferred for hemodialysis applications of the assembly 10, as they may increase the risk of vessel wall trauma and stenosis.

Referring to FIGS. 1 and 5–7, each of the catheters 26, 30 is configured to have a suitable length and width useful for insertion into the internal jugular vein 19 as described. The distal tip 68 and distal end region 52 of the second catheter 30 are proximally and longitudinally spaced from the distal tip 64 and distal end region 48 of the first catheter 26 by a sufficient distance d (shown in FIG. 1 and in FIG. 1a as d') which substantially prevents recirculation of the purified blood and blood to be purified. The distance d, is preferably about 4 centimeters, however, it should be understood by one of ordinary skill in the art, based on this disclosure, that d could be varied for different applications of the catheter assembly 10. Since blood flows toward the atrium, the blood flow in the internal jugular vein 19 is in a downward direction in FIGS. 5–7 as shown by the directional arrow in the vein 19. Thus, the distal end region 52 and distal tip 68 of the second catheter 30 may be characterized as being "downstream" from the distal end region 48 and distal tip 64 of the first catheter 26.

During use of the multiple catheter assembly 10 for hemodialysis, blood is preferably drawn out of the internal jugular vein 19 (i.e., the arterial flow) through the distal opening 80 of the second catheter 30 (downstream catheter) at the distal tip 68 and returned (i.e., the venous flow) through the distal opening 76 of the first catheter 26 through the distal tip 64 (upstream catheter). This flow direction is reversed from the conventional flow pattern of most prior art catheters and allows for higher flow rates in hemodialysis, as discussed immediately below. However, it should be understood by one of ordinary skill in the art, based on this disclosure, that the direction of flow can be reversed, in the manner of conventional flow patterns, such that blood is drawn from the upstream catheter's distal opening 76 and returned through the downstream catheter's distal opening 80.

By using the downstream lumen for drawing blood, the blood to be purified may be safely and efficiently drawn from an area closer to the right atrium of the heart in which the blood has a higher flow rate. This catheter assembly 10, like the SchonCath® catheter, is designed to function efficiently with new and effectively higher flow rate dialysis devices which have flow rates of about 450 cc/min. The ability to use higher flow rates without collapse of the lumens, as in multiple lumen catheters, decreases the time necessary for a patient to undergo conventional dialysis treatments, a significant patient benefit.

Referring to FIGS. 1 and 1a, the separation distance d, d' is preferably about 4 centimeters. This separation distance d is longer than the traditional spacing of return and intake openings of most multiple lumen catheters which is typically about 2 centimeters. The preferred longer distance d helps to prevent recirculation of purified blood returned upstream through the lumen 28 with blood to be purified being drawn through the lumen 32. By having at least a portion of the distal end regions 48, 52 move freely in the vessel 19, 360° flow through the individual catheters for both venous and arterial flow can be achieved thereby eliinating arterial and venous insufficiency caused by occlusion against the vessel walls.

As best shown in FIGS. 1, 5 and 7, it is preferred that the distal end regions 48, 52 be provided with a plurality of apertures 74, 74'. In FIG. 1a, these apertures 74", 74'" are preferably located in the portion of the distal end regions 48', 52' which includes a generally circular cross section. Further, providing apertures helically and circumferentially around the distal end regions 48, 52 of the embodiments of FIG. 1 and 1a prevents sucking of the first and second catheters 26, 30 against the blood vessel, and minimizes vibratory movement of the distal end regions 48, 52 by equalizing the disturbances of intake and return flow through the apertures 74, 74'. Minimizing the vibratory movement helps prevent stenosis. The apertures 74, 74' also provide alternative openings in the distal end regions 48, 52 of the catheters 26, 30 such that if flow becomes blocked at an opening 76 or 80, dialysis can continue while a replacement catheter assembly is being provided.

An important feature of the invention is that prior to insertion of the multiple catheter assembly into the area 12, the split distal end regions 48, 52 of the first and second catheters 26, 30 are at least partially unattached from each other, and preferably are fully unattached. The unattached portions of the distal end regions of the catheters 26, 30 are thus freely movable within the jugular vein 19 with respect to each other.

In the embodiment of the invention described above, the first and second catheters 26 and 30 are fabricated with a separation distance d, and the distal end regions 48, 52 are split from each other prior to use a distance of about three centimeters as measured longitudinally from the distal tip 64 of the first catheter 26, which, in this embodiment is the shorter catheter. This facilitates forming the openings 74, 74' in the distal end regions 48, 52. However, the distal end regions 48, 52 may be split from each other by greater or lesser amounts as described below. If desired, and as preferred in general use, the entire length of the catheters 26, 30 in the cannulating portion 20 may be split from each other up to the hub 24.

While there is preferably a separation distance d between distal tips 64, 66 of catheters 26, 30, the distal tips may be flush with each other. If the catheters 26, 30 include distal end regions 48, 52 having apertures 74, 74', the distal end regions of the catheters 26, 30 are preferably split, for use, at least a length sufficient to allow flow into and out of all apertures 74, 74' and more preferably, the full length of the cannulating portion 20.

Referring to FIGS. 1 and 2, the hub 24 and extension tubes 84, 90 are now explained in detail. However, it should be understood, based on this disclosure that a hub 24 and extension tube portion 22 of the catheter is optional. The splittable catheter of the present invention can be formed simply as at least two splittable catheter tubes. The proximal tips of the catheters could be made connectable to dialysis equipment or other apparatus by providing luers or other connectors to the proximal tips of the catheters without a hub or additional extension tubes. In the preferred embodiment as shown, however, such as hub and extension tubes are provided and are described below.

As discussed above, the cannulating portion 20 of the assembly 10 is preferably joined to the extension tube portion 22 in the hub 24. As shown in FIGS. 1 and 2, the extension tube portion 22 includes a first extension tube 84 having a distal end 86 and a proximal end 88, and a second extension tube 90 having a distal end 92 and a proximal end 94. The proximal ends 88, 94 are shown in FIG. 1, and the distal ends 86, 92 are shown in FIG. 2. The extension tube distal ends 86, 92 and the respective proximal openings 78, 82 of the catheters 26, 30 are brought into fluid communication with each other via tunnels 116, 118 molded in the hub 24. The extension tube proximal ends 88, 94 are preferably connected to respective female luer locks 96, 98 in a conventional manner. If desired, the female luer locks 96, 98 may be substituted with any suitable type of quick connect fittings, ferrule connectors, threadable connector, and the like.

Accordingly, the first and second catheters 26, 30 are in fluid communication with respective first and second extension tubes 84, 90. The hub 24 preferably includes a suture wing 102 for securing the assembly 10 to the body 14, if desired, for example for acute catheterizations.

In one preferred embodiment of the present invention, the cannulating portion 20 of the assembly 10 is fabricated by a single extrusion process, injection molding process, or blow molding process. The preferred fabrication process is extrusion. In such processes, the membrane 46 will be formed using the same material as the catheters 26, 30. In an alternative embodiment, each catheter 26, 30 and the membrane 46 are individually formed, and then joined by suitable manufacturing techniques to become a unitary product. In this alternative process, the membrane 46 may be formed of the same, or different material than the catheters 26, 30. The membrane 46 should be made of a biocompatible plastic or elastomer, more preferably from a biocompatible elastomer. Examples of biocompatible elastomers are described above with respect to the catheters 26, 30.

FIGS. 5–7 will now be used to describe preferred methods of inserting a catheter according to the present invention. FIG. 5 illustrates a method particularly preferred for acute catheterization. FIGS. 6 and 7 illustrate a method particularly preferred for chronic catheterization.

Referring now to the acute catheterization procedure of FIG. 5, an incision 110 is initially made near an insertion site 112 which is to be aspirated with a syringe or other introducer apparatus near or proximate the area to be catheterized 12. If the catheter assembly 10 is used for hemodialysis and the area to be catheterized 12 is the internal jugular vein 19, the incision 110 is made in the clavicular triangle region, as shown for example, in FIG. 5. The exact location of the incision 110 can be varied by the physician. In accordance with the Seldinger technique, a narrow needle is inserted through the incision 110 and into the vein 19, and the vein aspirated. A guide wire is then passed through the needle, or other introducer, and the needle is removed. A dilator (not shown) and a tearable sheath are introduced over the guide wire and partially into the vein 19. While the sheath is not shown in FIG. 5, the sheath as used in the acute method is then same as the sheath 114 as shown in FIG. 7 with respect to the following description of the chronic method. Once the sheath is in place, the guide wire is removed. The insertion site 112 is now ready to accept the catheter assembly 10.

Prior to insertion, the catheter assembly 10 of FIG. 1 is split along the splittable membrane 46 from the distal tip 64 of the first catheter 26 by a longitudinal distance which is at least long enough to allow free flow through all openings 74, 74'. Preferably, the membrane 46 is split along the full length of the catheters 26, 30 up to the hub 24. If a fabric tissue ingrowth cuff is provided to the outer surface of the cannulating portion 20 for use in subcutaneous securement, the membrane 46 is preferably split up to the fabric tissue ingrowth cuff. Preferably, the catheters 26, 30 are already at least partially split along a portion of the distal end regions 48, 52 of the catheters 26, 30 as shown in FIG. 3, prior to use which facilitates splitting of the catheter assembly membrane 46. While the user does not have to split the entire length of the membrane 46, it is preferred that the membrane be fully split for allowing independent movement within the vessel.

After splitting, the distal end regions 48, 52 of the first and second catheters 26, 30 are inserted into, and through, the sheath in juxtaposed relationship. The distal end regions 48, 52 are inserted until they are properly positioned within the area 12, as shown in FIG. 5. The sheath is then removed in the conventional manner, leaving the distal end regions 48, 52 of the first and second catheters 26, 30 in the area 12. As shown in FIG. 5, at least a portion of the distal end regions 48, 52 of each of the catheters 26, 30 may freely move within the area 12.

Next, the incision 110 is closed and the proximal end regions 50, 54 are secured to an external surface 18 of the body 14 by fastening material 56, such as adhesive tape. Alternatively, the incision 110 may be closed after securement. While not necessary in acute catheterization, tunnelling and subcutaneous securement can be effected by use of a trocar as discussed below with respect to chronic catheterization. The open ends of the luer locks 96, 98 are connected in fluid communication to respective fluid inlets and outlets of a hemodialysis unit, or other fluid transfer equipment (not shown) and dialysis may now begin.

The chronic catheterization procedure is now described with respect to FIGS. 6 and 7. Referring to FIG. 6, the unseparated portion of the assembly 10 may be located within a subcutaneous tunnel 58 in the subcutaneous area 16 of the body 14, using various tunnelling techniques. In one technique, the distal end regions 48, 52 of the catheters 26, 30 are pulled through the tunnel 58 from the caudal end of the tunnel, while forming the tunnel using a trocar or other tunnelling tool, leaving the proximal end regions 50, 54 at least partially within the tunnel 58 and the distal end regions 48, 52 extending outwardly from the opposite end of the tunnel 58 near the area to be catheterized 12. The membrane 46 would then be split for the portion of the catheter extending outwardly from the tunnel. Alternatively, and preferably, the membrane 46 is split prior to tunneling. One technique for tunnelling the split catheters 26, 30 through a subcutaneous area when the catheters are already split, includes an elastomeric tube. A tunneling tool, e.g., a trocar, is generally already equipped with a 3 or 4 in (7.62 to 10.16 cm) elastomeric safety tube over its pointed, cutting end (not shown). If the trocar does not already have such a tube, any similar tube may be used in conjunction with the trocar. The safety tube may be slid down the trocar to capture the ends of the catheters. Preferably, the gripping end of the trocar is first inserted into the lumen of the venous catheter 26. The tube may then be slid over the connected trocar and catheter to also capture a portion of the distal end region 52 of the arterial catheter 30. Using either technique, the connected trocar and catheters 26, 30 are pulled through a subcutaneous tunnel made by the pointed end of the trocar. Once the catheters have been placed in the subcutaneous area, and prior to inserting the distal end regions 48, 52 into the area to be catheterized 19, the catheters 26, 30 appear as shown in FIG. 6.

If the catheters were subcutaneously tunnelled without first splitting the membrane, the catheters should be split prior to insertion into the area to be catheterized. However, it is preferred that the membrane 46 be split prior to subcutaneous tunneling.

Referring now to FIGS. 6 and 7, an incision 110 is made at the insertion site 112, either before or after tunnelling, and the distal end regions 48, 52 of the first and second catheters 26, 30 are inserted into, and through, the sheath 114 in a juxtaposed manner, in the same manner as described above with respect to FIG. 5. The remaining catheter insertion and incision closure steps are the same as those described above with respect to FIG. 5.

After the catheter assembly 10 is inserted as shown in FIG. 7, the incision is closed and the cannulating portion 20 of the assembly 10 is substantially below the skin of the patient. Lastly, the open ends of the luer locks 96, 98, extending caudally from the tunnel, are attached in fluid communication with respective fluid inlets and outlets of a hemodialysis unit, or other fluid transfer equipment (not shown), and dialysis can begin.

To further ensure that the proximal catheter end regions 50, 54 remain secured in the subcutaneous area 16 of the body 14, one or more anchoring members, such as a tissue ingrowth cuff (not shown) may be positioned around (i.e., circumferentially disposed on) the proximal end regions 50, 54, such that the anchoring members will be situated in the subcutaneous area 16 after tunnelling, as is well-known in the prior art. If such a cuff is used, the catheters 26, 30 are only split along the membrane 46 up to the cuff and not to the hub 24.

The present invention provides the advantages of a Tesio or SchonCath® catheter, in that it has two freely movable distal tips, while also providing the advantages of a single insertion method, and the ability to easily manipulate the proximal end regions of the catheter and tunnel the catheters with only one tunnelling procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A multiple catheter assembly, comprising:
   (a) a first catheter having a proximal tip, a distal end region terminating in a distal tip, and an outer surface defining at least a first lumen extending longitudinally therethrough between a distal and a proximal opening;
   (b) a second catheter having a proximal tip, a distal end region terminating in a distal tip, and an outer surface defining at least a second lumen extending longitudinally therethrough between a distal and a proximal opening, wherein the first lumen and the second lumen are independent from each other for facilitating simultaneous flow in opposite directions; and (c) a splittable membrane joining the outer surfaces of both the first and second catheters for allowing the first and second catheters to be at least partially longitudinally split from each other.

2. The multiple catheter assembly according to claim 1, wherein the first and second catheters have a generally semi-circular cross section, the first catheter comprises a generally flat side surface, and the second catheter comprises a generally flat side surface.

3. The multiple catheter assembly according to claim 2, wherein the membrane extends longitudinally between the generally flat side surface of the first catheter and the generally flat side surface of the splittable second catheter, and the splittable membrane has a cross-sectional length which is significantly smaller than an outer diameter of said multiple catheter assembly as measured transversely across said multiple catheter assembly.

4. The multiple catheter assembly according to claim 2, wherein the distal end regions of the first and second catheters each have a generally circular cross section, and the outer surfaces of the first and the second catheters are rounded inwardly at a point of transition along each of the first and second catheters between the generally semi-cylindrical cross sections of the catheters and the generally circular cross sections of the distal end regions.

5. The multiple catheter assembly according to claim 1, wherein the first catheter has a first length as measured longitudinally between said distal and proximal tips of said first catheter and the second catheter has a second length as measured longitudinally between said distal and proximal tips of said second catheter, wherein said second length is longer than said first length.

6. The multiple catheter assembly according to claim 1, wherein the proximal tips of the first and second catheters are substantially aligned with each other and the distal tips are longitudinally spaced from each other.

7. The multiple catheter assembly according to claim 6, wherein the distal tips are longtudinally spaced a distance sufficient to prevent recirculation of fluid passing through the distal opening of the first catheter in a first flow direction and fluid passing through the distal opening of the second catheter in a second flow direction opposite to the first direction.

8. The multiple catheter assembly according to claim 1, wherein the first and second catheters are identical in cross section.

9. The multiple catheter assembly according to claim 1, wherein the assembly further comprises a third catheter having an outer surface defining at least a first longitudinally extending lumen and a second splittable membrane joining the outer surface of the first catheter and the outer surface of the third catheter.

10. The multiple catheter assembly according to claim 9, wherein the assembly further comprises a third splittable membrane extending longtudinally between the outer surface of the second catheter and the outer surface of the third catheter.

11. The multiple catheter assembly according to claim 1, further comprising a first proximally extending extension tube in fluid communication with the proximal opening of the first catheter and a second proximally extending extension tube in fluid communication with the proximal opening of the second catheter.

12. The multiple catheter assembly according to claim 11, wherein the first and second catheters are attached to the respective first and second extension tubes by a hub.

13. The multiple catheter assembly according to claim 1, wherein the first catheter comprises an internal longitudinally extending septum dividing said first lumen.

14. The multiple catheter assembly according to claim 1, wherein a plurality of apertures is arranged circumferentially around each of the distal end region of the first catheter and the distal end region of the second catheter.

15. A method for inserting a multiple catheter assembly into an area of a body to be catheterized, the multiple catheter assembly comprising (i) a first catheter having a proximal end region terminating in a proximal tip, a distal end region terminating in a distal tip, and an outer surface defining at least a first longitudinally extending lumen, (ii) a second catheter having a proximal end region terminating in a proximal tip, a distal end region terminating in a distal tip, and an outer surface defining at least a second longitudinally extending lumen, wherein the first lumen and the second lumen are independent from each other for facilitating simultaneous flow in opposite directions, and (iii) a splittable membrane joining the outer surfaces of both the first and second catheters, the method comprising the steps of:

(a) making an incision near the area to be catheterized;

(b) at least partially splitting the distal end regions of the first catheter and the second catheter from each other by splitting the splittable membrane; and (c) inserting the distal end regions of the first and second catheters in juxtaposed relation through the incision and into the area to be catheterized.

16. The method according to claim 15, further comprising inserting a tearable sheath into the area to be catheterized prior to step (c), and wherein step (c) further comprises inserting the distal end regions through the sheath and into the area to be catheterized.

17. The method according to claim 16, further comprising removing the sheath after the distal end regions of the first and second catheters are in the area to be catheterized.

18. The method according to claim 15, further comprising closing the incision after the distal end regions are inserted in the area to be catheterized.

19. The method according to claim 15, further comprising securing the proximal end regions of the first and second catheters to the body.

20. A method for inserting a multiple catheter assembly into an area of a body to be catheterized, the multiple catheter assembly comprising (i) a first catheter having a proximal end region terminating in a proximal tip, a distal end region terminating in a distal tip, and an outer surface defining at least a first longitudinally extending lumen, (ii) a second catheter having a proximal end region terminating in a proximal tip, a distal end region terminating in a distal tip, and an outer surface defining at least a second longitudinally extending lumen, wherein the first lumen and the second lumen are independent from each other for facilitating flow in opposite directions, and (iii) a splittable membrane joining the outer surfaces of both the first and second catheters, the method comprising the steps of:

(a) subcutaneously moving the first and second catheters through a tunnel formed in the body by pulling the distal end regions through the tunnel and outwardly therefrom near the area to be catheterized, leaving the proximal end regions at least partially within the tunnel;

(b) making an incision near the area to be catheterized;

(c) at least partially splitting the distal end regions of the first and the second catheters from each other by splitting the splittable membrane; and (d) inserting the distal end regions of the first and second catheters in juxtaposed relation through the incision and into the area to be catheterized.

21. The method according to claim 20, further comprising inserting a tearable sheath into the area to be catheterized prior to step (d), and wherein step (d) further comprises inserting the distal end regions through the sheath and into the area to be catheterized.

22. The method according to claim 21, further comprising removing the sheath after the distal end regions of the first and second catheters are in the area to be catheterized.

23. The method according to claim 20, further comprising closing the incision after the distal end regions are inserted in the area to be catheterized.

24. The method according to claim 20, further comprising securing the proximal end regions of the first and second catheters within the tunnel.

* * * * *